Figure 1:
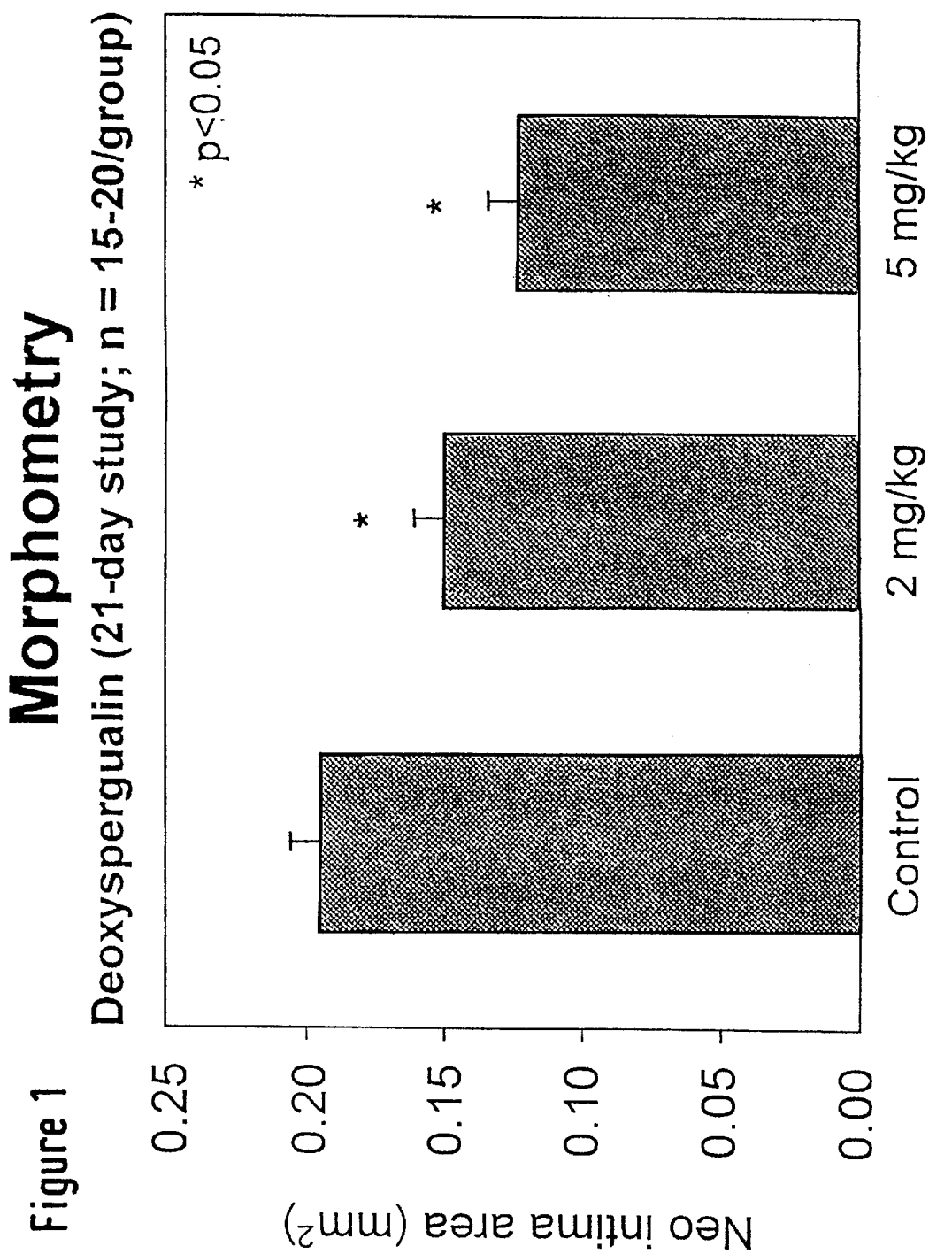

United States Patent [19]
Lindner et al.

[11] Patent Number: 5,849,799
[45] Date of Patent: Dec. 15, 1998

[54] USE OF DEOXYSPERGUALIN FOR PREPARING A PHARMACEUTICAL FOR TREATING HYPERREACTIVE INFLAMMATORY DISEASES

[75] Inventors: Jürgen Lindner, Marburg; Gerhard Dickneite, Marburg-Cappel; Hans-Ulrich Schorlemmer, Marburg-Dagobertshausen; Klaus Bosslet, Marburg, all of Germany

[73] Assignee: Behringwerke Aktiengesellschaft, Marburg, Germany

[21] Appl. No.: 406,406

[22] Filed: Mar. 20, 1995

[30] Foreign Application Priority Data

Mar. 22, 1994 [DE] Germany .......................... 44 09 804.9
May 3, 1994 [DE] Germany .......................... 44 15 553.0

[51] Int. Cl.⁶ ........................ A61K 31/155; A61K 31/16; A61K 31/415
[52] U.S. Cl. ............................ 514/634; 514/579
[58] Field of Search ..................... 514/310, 579, 514/634; 564/230, 240

[56] References Cited

U.S. PATENT DOCUMENTS

| | | | |
|---|---|---|---|
| 4,778,824 | 10/1988 | Umezawa et al. ................... | 514/626 |
| 4,847,299 | 7/1989 | Dickneite et al. ................... | 514/579 |
| 4,851,446 | 7/1989 | Umezawa ............................. | 514/620 |
| 5,238,689 | 8/1993 | Dwyer et al. ........................ | 424/617 |

FOREIGN PATENT DOCUMENTS

4329503A1 3/1995 Germany .

OTHER PUBLICATIONS

The Merck Manual, 16th Edition, Edited by Berkow et al., Published in 1992, pp. 834–839.

Okayasu et al., "A Novel Method In The Induction Of Reliable Experimental Acute And Chronic Ulcerative Colitis In Mice", *Gastroenterology*, vol. 98:694–702, (1990).

Schorlemmer et al., "Preclinical Studies With 15–Deoxyspergualin In Various Animal Models For Autoimmune Diseases", *Immunomodulating Drugs*, vol. 685:155–174, (1993).

*Primary Examiner*—Robert H. Harrison
*Attorney, Agent, or Firm*—Foley & Lardner

[57] ABSTRACT

Methods are disclosed for treatment of hyperreactive inflammatory diseases of humans and animals comprising administering a pharmaceutically effective amount of deoxyspergualin to a human or an animal.

10 Claims, 1 Drawing Sheet

USE OF DEOXYSPERGUALIN FOR PREPARING A PHARMACEUTICAL FOR TREATING HYPERREACTIVE INFLAMMATORY DISEASES

The invention relates to the use of deoxyspergualin for preparing a pharmaceutical for the therapy and prophylaxis of hyperreactive inflammatory diseases in humans and animals.

Hyperreactive inflammatory diseases are defined by the fact that the body reacts to nonspecific stimuli with an overshooting inflammatory reaction. This overshooting inflammatory reaction (hyperreactivity) results in pathological changes which lead to these syndromes developing and becoming chronic. Syndromes which are caused by hyperreactivity are chronic inflammatory intestinal diseases, hyperreactive, obstructive respiratory tract diseases, inflammatory vascular diseases, pancreatitis, sepsis and hyperreactive inflammatory encephalopathies, such as Alzheimer's disease.

An example of a chronic inflammatory intestinal disease is ulcerative colitis. The pathogenesis of this disease has not been elucidated. However, it seems certain that nonspecific, acute inflammatory reactions (e.g. due to foodstuff noxae or infections) play a causative role in this disease. As a consequence of this primary inflammatory reaction, the barrier function of the colon epithelium is destroyed. This permits noxae from the intestinal lumen (e.g. toxins of anaerobic organisms, especially Clostridia) to act directly on unprotected tissue, thereby further intensifying the disease process and rendering it chronic. It is then said that hyperreactivity has been established. This hyperreactivity is expressed not only in a chronic inflammatory reaction but also in severe tenesma, which are characteristic of this syndrome. The current therapy for ulcerative colitis principally comprises administering anti-inflammatory substances such as 5-aminosalicylic acid or antibiotics/chemotherapeutics such as metronidazole or some sulfonamide derivatives.

Bronchial asthma is an example of what is understood by a hyperreactive obstructive respiratory tract disease. Bronchial asthma is a disease which is characterized by attacks of dyspnoea (bronchial hyperreactivity), accompanied by the signs of a bronchial obstruction which, between the attacks, is wholly or partially reversible either spontaneously or as a result of treatment. In the hyperreactive bronchial tree which is typical for asthma, nonspecific and specific stimuli lead to the triggering of "asthma attacks". Mucosal edema, bronchospasm and dyscrinism are the triad which characterizes asthmatic bronchial obstruction. The cause of the hyperreactivity of the bronchial system is rooted in damage to the mechanisms which protect the lung against noxae. Ciliary epithelium and mucus are responsible for removing harmful substances from the lung before they result in damage to the lung tissue and the development of an inflammatory reaction. Damage to the ciliary epithelium and perturbations in the composition of the bronchial mucus are found in asthma. As a result, it is no longer possible to eliminate harmful substances adequately and an inflammation develops. In association with this inflammatory process, the protective and barrier functions of the lung are further disrupted. "Harmless" substances can penetrate more deeply into the tissue and there give rise, by nonspecific irritation (e.g. as a result of phagocytosis by macrophages and, subsequent liberation of mediators), to further intensification of the inflammatory reaction and consolidation of its chronic nature.

As can be observed generally in inflammatory processes, the stimulatory threshold (e.g. of nerve fibers) is also lowered in the case of asthma. This is designated hyperreactivity of the bronchial tree. It is evident, therefore, that a wide variety of noxae, as listed below, can give rise to an asthma attack:

infections of the upper and lower respiratory tracts, physical and chemical inhalation noxae (smoke, dust, vapors, smogs, rapid temperature changes and gases), physical exertion, psychic strain (conscious or unconscious);

medicaments (e.g. indomethacin, which increases leukotriene synthesis);

Arteriosclerosis is an example of a chronic inflammatory vascular disease. Arteriosclerosis is a pathological change in the arteries, involving hardening, thickening, loss of elasticity and loss of lumen. The pathogenesis of arteriosclerosis has not been finally elucidated. However, it appears certain that a wide variety of noxae (e.g. hypertension, cigarette smoke inhalation, hyperlipidemia, metabolic condition in diabetes, or hyperuricemia) give rise to a nonspecific inflammatory process. This primary, inflammatory process is responsible for the development of "hyperreactivity" of constituents of the blood and/or of the blood vessel wall. If the noxae which trigger the condition persist over a relatively long period of time, the inflammatory reaction then becomes chronic and self-perpetuating, so that this process persists, even later when the noxae eliciting it are no longer present. One of these eliciting noxae can, for example, be turbulent flow conditions in certain parts of the vascular system (e.g. branching of the common carotid artery from the aortic arch). As a result of the mechanical stresses caused by the turbulent flow, mediators are released both from the vessel wall and from the cellular constituents of the blood. These mediators give rise to the manifestation of arteriosclerosis by way of a nonspecific inflammatory reaction and the hyper-reactivity associated with this reaction.

Platelet derived growth factor, epidermal growth factor, thromboxane and prostaglandins are only some of the mediators which, together with metabolic and cellular reactions in the vessel wall, can be observed in association with this inflammatory change. These processes result in intimal edema, increase in the synthesis of acidic mucopolysaccharides, precipitation of lipoproteins, fibrinogen or albumin, and proliferation of connective tissue cells and muscle cells together with increased synthesis of collagen and elastin (fibrosis, elastase). At an advanced stage, these alterations of the vessels appear macroscopically as calcification.

Even today, the therapy of the above-described hyperreactive inflammatory diseases must be considered to a large extent inadequate. No adequate therapeutic options exist for Alzheimer's disease, pancreatitis or sepsis. The severe side effects of the drugs employed represent an especially serious problem for the patient. Consequently, it is a medical necessity to develop drugs for the therapy of inflammatory diseases which are more active but which have fewer side effects.

We have now found, unexpectedly, that 15-deoxyspergualin [(±)-1-amino-19-guanidino-11-hydroxy-4,9,12-triazanonadecane-10,13-dione trihydrochloride; DSG], exhibits strong activity in various hyperreactive/inflammatory animal models. This finding is all the more unexpected in that the substance has been known for years and in recent years has been described by several research groups as an immunosuppressive substance for treating transplantation crises and various autoimmune diseases (Immunomodulating Drugs, 685. 155–174; 1993).

While it can be expedient to use the racemate, the active stereoisomer can also be employed.

The efficacy of DSG for treating humans and animals is demonstrated by the following experimental animal systems in which drugs which have been employed successfully in human medicine are also active. DSG may also advantageously be employed in combination with other drugs. These drugs are: metronidazole, 5-aminosalicylic acid, salazosulfapyridine, sulfapyridine, antibiotics generally, chemotherapeutic agents generally, cyclosporin A, FK 506, immunomodulators generally, budesonide, prednisone, prednisolone, fluocortolone, glucocorticoids generally, azathioprine, methotrexate, mycophenolate mofetil, brequinar, immunosuppressive agents generally, isoprenaline, orciprenaline, β-sympathomimetics generally, theophylline, phosphodiesterase inhibitors generally, ipratropium bromide, atropine, parasym patholytic agents generally, ketotifen, cromoglycic acid, mast cell stabilizers generally, ambroxol, carbocisteine, secretolytic agents generally, acetylcysteine MESNA, mucolytic agents generally, clemastine, terfenadine, antihistaminics generally, reserpine, guanfacine, clonidine, pindolol, β-receptor blockers generally, prazosin, minoxidil, diazoxide, nifedipine, verapamil, captopril, ACE inhibitors generally, furosemide, diuretics generally, nitroglycerin, isosorbide dinitrate, antihypertensive agents generally, vasodilatory agents generally, acetylsalicylic acid, diclofenac, phenylbutazone, heparin, antithrombotic agents generally and anti-inflammatory agents generally (also non-steroidal anti-inflammatory agents).

DSG may be administered orally, intravenously, subcutaneously, intraperitoneally, percutaneously, cutaneously, topically, by inhalation, intramuscularly, intrathecally, intraocularly, ocularly, buccally, nasally or rectally, and in a dose of from 0.1 to 100 mg/kg, preferably intravenously or else orally.

Examples of hyperreactive inflammatory diseases are ulcerative colitis, asthma, arteriosclerosis, pancreatitis, sepsis or Alzheimer's disease.

The following examples elucidate the invention.

EXAMPLES

Ulcerative colitis was induced with dextran sulfate in accordance with the method of I. Okayasu et al. (Gastroenterology, 1990, 98: 694–702). The following parameters were monitored as parameters indicating the course of the ulcerative colitis:

- appearance of blood in the stools; (% of positive animals on the last day of the experiment);
- shortening of the colon: (parameter measured: length of the colon in cm);
- histological changes; (scoring index: 0=no pathological findings to 8=most severe pathological changes such as ulcerations, crypt abscess, massive inflammatory infiltrate)

Example 1
Intraperitoneal administration of DSG
Experimental groups
  I. Negative control (healthy animals, no colitis, N=10);
  II. Positive control (animals with colitis, no treatment, N=10)
  III. 5 mg of DSG/kg (animals with colitis, treatment from day 0 to 9, N=10)
  IV. 7.5 mg of DSG/kg (animals with colitis, treatment from day 0 to 9; N=10)
  V. 10 mg of DSG/kg (animals with colitis, treatment from day 0 to 9, N=10)
  VI. 12.5 mg of DSG/kg (animals with colitis, treatment from day 0 to 9; N=10)
  VII. 15 mg of DSG/kg (animals with colitis, treatment from day 0 to 9; N=10)

| Treatment group: | I: | II: | III: | IV: | V: | VI: | VII: |
|---|---|---|---|---|---|---|---|
| Blood in the stools: [% positive] | 0% | 100% | 80% | 70% | 50% | 30% | 10% |
| Length of the colon: [cm] | 6.9 ± 0.2 | 4.8 ± 0.3 | 5.1 ± 0.5 | 5.5 ± 0.4 | 5.7 ± 0.4 | 5.8 ± 0.6 | 6.1 ± 0.5 |
| Histology [scoring index] | 0 | 4.5 ± 1.1 | 4.2 ± 0.7 | 3.4 ± 0.6 | 3.1 ± 0.8 | 2.9 ± 0.6 | 2.7 ± 0.8 |

Example 2
Inttaperitoneal administration of DSG
Experimental groups
  I. Negative control (healthy animals, no colitis, N=10);
  II. Positive control (animals with colitis, without treatment, N=10);
  III. Metronidazole (animals with colitis, 0.2 mg/ml, treatment from day 0 to 9, N=10);
  IV. Metronidazole (animals with colitis, 0.5 mg/ml, treatment from day 0 to 9, N=10);
  V. 7.5 mg of DSG/kg (animals with colitis, treatment from day 0 to 9; N=10);
  VI. 10 mg of DSG/kg (animals with colitis, treatment from day 0 to 9; N=10);
  VII. 7.5 mg of DSG/kg in combination with metronidazole, 0.2 mg/ml (animals with colitis, treatment from day 0 to 9, N=10);
  VIII. 10 mg of DSG/kg in combination with metronidazole, 0.5 mg/ml (animals with colitis, treatment from day 0 to 9, N=10);

| Treatment group: | I: | II: | III: | IV: | V: | VI: | VII: | VIII: |
|---|---|---|---|---|---|---|---|---|
| Blood in the stools: [% positive] | 0% | 100% | 80% | 10% | 60% | 40% | 10% | 0% |
| Length of the colon: [cm] | 6.9 ± 0.4 | 4.9 ± 0.3 | 5.7 ± 0.9 | 6.0 ± 0.5 | 5.7 ± 0.7 | 5.9 ± 1.0 | 6.2 ± 0.5 | 6.9 ± 0.9 |
| Histology [scoring index] | 0 | 4.1 ± 0.7 | 2.9 ± 1.1 | 2.4 ± 1.2 | 3.6 ± 1.6 | 2.1 ± 1.1 | 2.2 ± 1.6 | 1.0 ± 0.5 |

Example 3
Oral administration of DSG
Experimental groups
  I. Negative control (healthy animals, no colitis, N=10);
  II. Positive control (animals with colitis, without treatment, N=10);
  III. 10 mg of DSG/kg (animals with colitis, treatment from day 0 to 9; N=10);
  IV. 20 mg of DSG/kg (animals with colitis, treatment from day 0 to 9; N=10);
  V. 40 mg of DSG/kg (animals with colitis, treatment from day 0 to 9, N=10);

| Treatment group: | I: | II: | III: | IV: | V: |
|---|---|---|---|---|---|
| Blood in the stools: [% positive] | 0% | 80% | 60% | 40% | 20% |
| Length of the colon: [cm] | 7.8 ± 0.4 | 5.5 ± 0.5 | 5.9 ± 0.7 | 6.3 ± 0.4 | 7.1 ± 0.8 |
| Histology [scoring index] | 0 | 3.9 ± 0.6 | 3.1 ± 0.8 | 2.7 ± 0.7 | 2.4 ± 0.7 |

Example 4
Effect of DSG on IgE synthesis in the rat (model disease for asthma)

In this example, an investigation was carried out to determine whether the elevation of the plasma level of IgE which is characteristic of asthma can be suppressed by DSG. For this purpose, Brown-Norway rats were treated with $HgCl_2$ (1 mg/kg subcutaneously, 3×/week). The IgE level in the plasma was determined using the ELISA technique; the table shows the extinctions ($E_{450}$ nM) which were measured and which are proportional to the IgE levels.

As the table shows, the IgE level in the $HgCl_2$ group (group 2) is clearly elevated as compared with the control (group 1) after 14 days. Administration of DSG (2 mg/kg, i.v., 1× daily, from day 0 to day 9) resulted in a distinct, significant suppression of the IgE level (group 3). These data permit the conclusion that DSG is effective in the therapy of asthma.

Table
Effect of DSG on $HgCl_2$-induced IgE synthesis in the Brown-Norway rat.

| Group | Plasma level of IgE ($E_{450}$ nm) |
|---|---|
| 1. Control | 0.23 ± 0.06 |
| 2. $HgCl_2$ treatment | 0.59 ± 0.14 |
| 3. $HgCl_2$ treatment 1 mg/kg DSG (d 0–9) | 0.29 ± 0.09* |

*p. < 0.05 (t-test)

Example 5
Effect of DSG on arteriosclerosis

An arteriosclerosis, characterized by the formation of neointima, was induced by balloon catheterization (PTCA) in the left carotid artery of male rats. DSG was administered to the PTCA rats in concentrations of 2 and 5 mg/kg from day 0 to day 21 (daily intraperitoneal administration). After the experiment was finished (day 21) the damaged artery was dissected out and the formation of neointima was measured morphometrically.

FIG. 1 shows that the formation of neointima, which is due to an arteriosclerotic lesion in the carotid artery, is significantly suppressed, in a dose dependent manner, by administering DSG.

We claim:

1. A method for the treatment of hyperreactive inflammatory diseases in a mammal comprising the administration of a pharmaceutically effective amount of deoxyspergualin to said mammal.

2. The method according to claim 1, wherein the active stereoisomer of said deoxyspergualin is used.

3. The method according to claim 1, wherein the disease is selected from the group consisting of a chronic inflammatory intestinal disease, a hyperreactive obstructive respiratory tract disease, a chronic inflammatory vascular disease and a chronic inflammatory disease of the brain.

4. The method according to claim 1, wherein the disease is selected from the group consisting of ulcerative colitis, asthma, arteriosclerosis, pancreatitis, sepsis and Alzheimer's disease.

5. The method according to claim 1, wherein said deoxyspergualin is administered with a second drug.

6. The method according to claim 1, wherein said deoxyspergualin is administered with metronidazole.

7. The method according to claim 1, wherein said deoxyspergualin is administered in a dosage of from 0.1 to 100 mg/kg.

8. The method according to claim 1, wherein said deoxyspergualin is prepared for peroral, intravenous, subcutaneous, intracutaneous, intraperitoneal, intrathecal, intraocular, ocular, buccal, nasal, percutaneous, cutaneous, topical, inhalative, intramuscular or rectal administration.

9. The method according to claim 1, wherein said deoxyspergualin is prepared for intravenous or oral administration.

10. The method according to claim 1, wherein said mammal is a human.

* * * * *